United States Patent [19]

Hornbeck

[11] 4,358,897
[45] Nov. 16, 1982

[54] GRAVITY GAUGE FOR DETERMINATION OF SHOULDER BONE ANGLES IN HORSES

[76] Inventor: William W. Hornbeck, 4785 Troth St., Mira Loma, Calif. 91752

[21] Appl. No.: 239,699

[22] Filed: Mar. 2, 1981

[51] Int. Cl.³ .......................... G01B 3/56; G01C 9/12
[52] U.S. Cl. .................................. 33/343; 33/174 D; 33/391
[58] Field of Search ................. 33/174 R, 174 D, 354, 33/343, 391, 471, 451, 340, 341, 342

[56] References Cited

U.S. PATENT DOCUMENTS 1,613,776  1/1927  Will ........................................ 33/354
3,047,957  8/1962  Conway ............................. 33/343 X Primary Examiner—Harry N. Haroian
Attorney, Agent, or Firm—Boniard I. Brown

[57] ABSTRACT

A gauge for the measurement of the shoulder bone angles of horses with respect to gravity, as an aid in the proper shoeing of the fore feet. The gauge has a gravity reference pointer which swings about a pivot axis so that it points downward under the influence of gravity, and protractor means to indicate the relative angle between the gravity pointer and the horse's shoulder bone angle. The protractor means include an angle scale, a concave locating cup adapted for positioning over the horse's shoulder point, an opposite bone angle pointer integral therewith and optional clamp means for controllably securing the gravity reference pointer with respect to the scale.

12 Claims, 5 Drawing Figures

GRAVITY GAUGE FOR DETERMINATION OF SHOULDER BONE ANGLES IN HORSES

CROSS REFERENCE TO RELATED APPLICATION

This case is related to U.S. patent application, Ser. No. 042,562 by William W. Hornbeck entitled, "Gauge for Determination of Shoulder Bone Angles in Horses" and filed May 25, 1979 now U.S. Pat. No. 4,262,424 and that application is hereby incorporated by reference as though fully set forth herein below.

BACKGROUND OF THE INVENTION

The present invention relates generally to apparatus for determining the shoulder angles of horses as an aid in proper shoeing, and more particularly such apparatus utilizing cup means for locating the measuring apparatus relative to the shoulder bone knot.

The hoof of the horse is a massive structure of keratinous tissue, corresponding to the nails and claws of other animals, which being without nerve endings and being abradable, is well adapted by the process of continuous growth and abrasion to be worn into a desirable or optimum configuration with respect to ground contact angle of the hoof for the particular horse, depending upon its weight, conformation, and preferred gait.

It has been known since ancient times that the load carrying and pulling capacity a of horse can be greatly increased by providing additional traction or grip at the hoof to ground contact. Therefore, the horse shoe as it is presently known has developed over the centuries, for the purposes of increasing the traction force exerted on the ground by the horse's muscular efforts, and to prevent hoof abrasion.

Because horse shoes are not abradable to adapt themselves to appropriate or optimum ground contact angles for particular horses, the horseshoes must be so mounted, for good results, as to be well-adapted to provide the desired ground contact angle in accordance with the conformation, weight and gait of a particular horse. This problem has long been known, and farriers and shoeing smiths have long known that it is preferrable to so shape and mount the shoe that the angle of the forefoot is parallel to the angle of the shoulder bone. Gauges for measuring hoof or forefoot angles have long been known, but the proper determination of correct hoof or forefoot angle with respect to the shoulder angle, has been dependent upon estimations involving guesswork. Prior shoulder angle measuring devices are described at page 100 of "*Horseshoeing Theory and Hoof Care*" by Dr. Niles Van Hoosen, et al. Such devices require considerable skill in the estimation of the run of the shoulder bone and in gauge manipulation, and have therefore not found wide acceptance.

SUMMARY OF THE INVENTION

The present gauge for determining the slope of a shoulder bone of a horse has shoulder bone locating means including at least one concave cup for positioning over the shoulder point and a bone angle pointer. A protractor with its angle scale is provided integral, with the concave cup and bone angle pointer. A gravity pointer which can rotate about a pivot axis fixed at the center of the protractor when subjected to gravity and released from the grip of optional releasable clamp means, is used to indicate the slope of the shoulder bone on the scale of the protractor.

In utilizing the gauge, the gravity pointer is released by the releasable clamp means for relative rotation to the protracter scale under the influence of gravity. The cup is positioned over the shoulder bone knot of the horse, the tip of the bone angle pointer being centered on the crest of the horse's withers and held in that position. The clamp means are tightened and the shoulder angle is read on the protractor by observing the point on the scale pointed to by the gravity reference pointer. The shoes of the horse can then be properly adapted and mounted to position of the hoofs in correct, corresponding angular relation to the ground.

In a modified form of the invention, two cups may be provided, facing in opposite directions to facilitate the measurement of both the left and right shoulder points of a horse, this being particularly important when the horse has an asymmetrical conformation requiring different shoe fittings for the left and right front hooves.

It is therefore an object of the invention to provide a shoulder-bone angle gauge for use in connection with horseshoeing, which permits quick and accurate determination of the shoulder conformation of a horse.

It is another object of the invention to provide such a gauge when couplings are utilized for location over a shoulder bone joint knot or shoulder point.

It is another object of the invention to provide such a gauge which is self aligning with gravity, no manipulation or levels being required.

These and other objects and advantages of the present invention will become apparent to those skilled in the art after considering the following detailed specification which discribes preferred embodiments thereof in conjunction with the accompanying drawing wherein:

BRIEF DESCRIPTION OF THE ACCOMPANYING DRAWING

DESCRIPTION OF THE PREFERRED EMBODIMENTS

Figure 1:
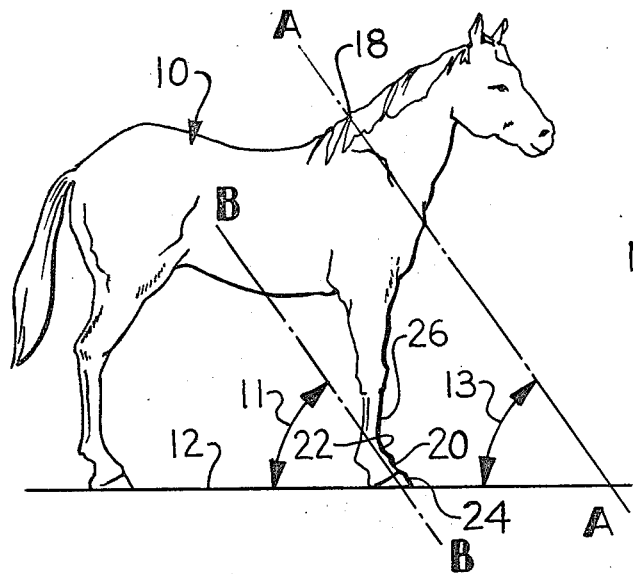
FIG. 1 is a side elevational view of a typical horse with indications of preferred shoulder and fore-hoof angles.
Figure 2:
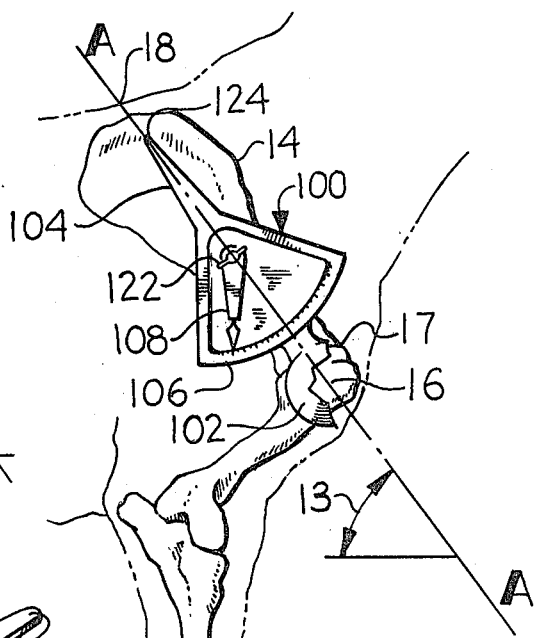
FIG. 2 is an enlarged, partial elevational view, showing a horse's shoulder, leg and hoof portions, with a shoulder gauge constructed according to the present invention in operative arrangement for gauging shoulder bone angle with a hoof gauge measuring parallel alignment of the forefoot with the shoulder angle thus determined.

Referring to FIGS. 1 and 2, a horse 10 is shown standing at rest with lines A—A and B—B indicating the angles of shoulder bone and the hoof respectively, the horse being shod in the proper manner. It will be noted that the lines A—A and B—B are parallel and, for horses of normal size and conformation, make an angle 11 with the ground 12 on the order of 52 to 57 degrees. The line A—A extends along the shoulder bone 14 of the horse 10 and is centered over a bony knot 16 at the lower shoulder joint 17, commonly known as the point of the shoulder. The upper end of the line A—A exits the horse's body at a point 18 known as the crest of the withers. These anatomical features are readily identified by all those skilled in the care of horses and define the run or angle 13, the shoulder bone 14 make with the ground 12.

The line B—B may be defined as extending along the axis of the horse's pastern 20, that portion of the foreleg interconnecting the hoof 24 with the fetlock 26. The line B—B parallels, with a high degree of reliability, the frontal angle 28 of the hoof 24, allowing a hoof gauge 30 of the prior art to be employed in determining the angle between line B—B and the ground 12.

FIG. 2 also shows a shoulder angle gauge 100 constructed in accordance with the present invention, measuring the alignment of the line A—A and of the underlying shoulder bone 14 to permit the adjustment of hoof 20 to the proper angle 28 to bring the horse's stance into proper balance. The gauge 100 has a cup 102 which is fitted over the shoulder bone knot 16, a bone angle pointer 104 aligned with the crest of the withers 18, and a reference protractor 106 integral therebetween. A gravity pointer is pivotally mounted with respect to the protractor 106 with its tip 110 in close proximity to the the angle scale 112 thereof. The gravity pointer 108 is weighted so that its tip 110 points toward the center of the earth under the influence of gravity. This is done by providing more mass on the tip side of the pointer 108 than on the opposite side thereof. The scale 112 includes graduations 114 properly calibrated to indicate the angle 13 of the shoulder bone 14 with respect to the ground 12.

Figure 3:
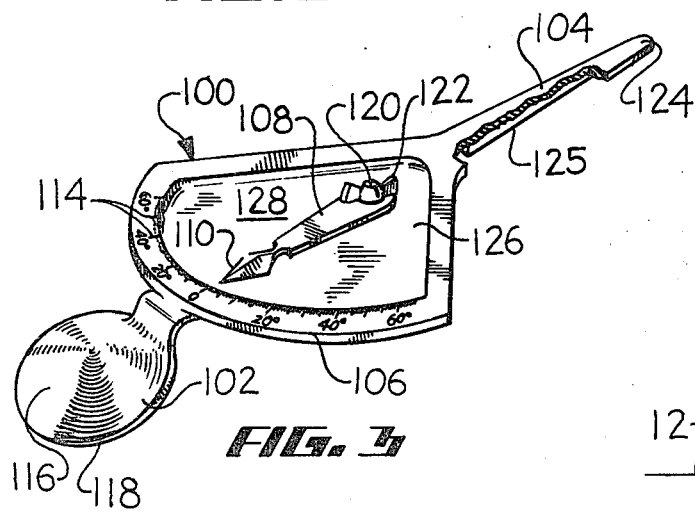
FIG. 3 is an enlarged perspective view of the shoulder angle gauge shown in FIG. 2.

FIG. 3 is a perspective, more detailed view of the gauge 100, showing the convex outer surface 116 of the cup 102 which has a matching concave inner surface 118 on the opposite side. The slope at the concave inner surface 118 is chosen to fit over the bony knot 16 of the point of the shoulder joint 17. As can be seen, the gravity pointer 108 is pivotally attached to the gauge 100 by a screw 120 and wing nut 122 so that by tightening or loosening the wing nut 122 the gravity pointer 108 can be made to swing free or be retained in a desired location for reading the protractor scale 112.

In use, the gauge 100 is applied by placing the cup 102 over the knot 16 of the shoulder joint 17, the center 123 of the cup 102 thus providing a fixed reference point on the horse's body. The bone angle pointer 104 and the cup 102 are rotated about the center 123 so as to position the tip 124 of the bone angle pointer 104 pointing at the crest of the withers 18. The wing nut 122 is loosened to permit the rotation of the gravity pointer 108 until it aligns with the vertical. Wing nut 122 is then retightened to maintain the relative alignment between the scale 112 of the protractor 106 and the tip 124 of the gravity pointer 106, and the gauge 100 is removed for a reading of the shoulder angle 13, by noting the position of tip 124 with respect to the scale 112. The hoof gauge 30 then may be set to the corresponding angle, and the shoe, or shims between the shoe and the distal surface of the hoof, adjusted until the desired angle of the hoof 24 is attained.

Figure 4:
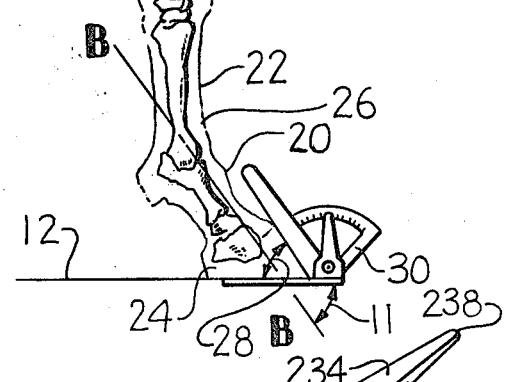
FIG. 4 is a partially cutaway side view of a portion of the gauge of FIG. 3.
Figure 5:
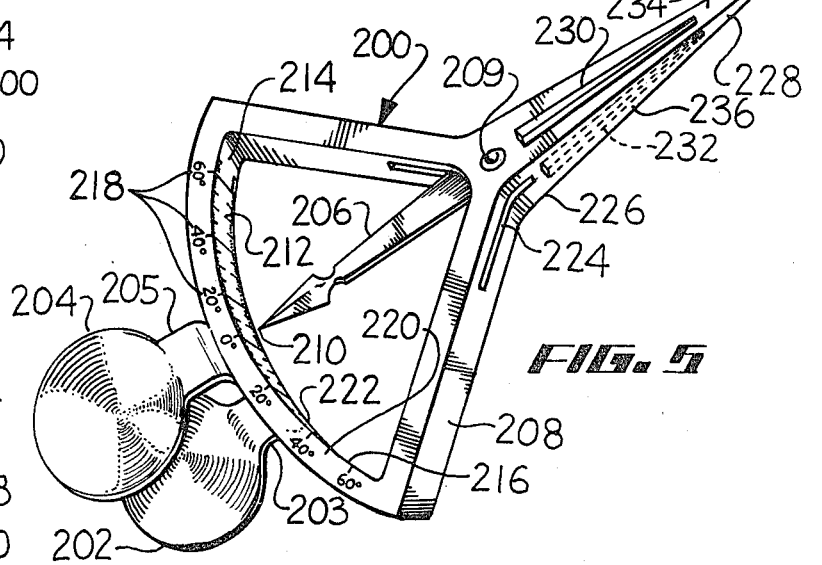
FIG. 5 is a perspective view of another embodiment of the horse shoulder angle gauge of the invention, wherein two locating cups are defined for gauging right and left shoulder bones.

FIG. 4 is a side view of the angle gauge 100, showing the position of the cup 102 relative to the protractor 106, the gravity pointer 108, the screw 120, the wing nut 122 and a portion of the bone angle pointer 104. As can be seen, the gravity pointer 108 is positioned in a triangular cavity 126 of the portractor with a thin back wall 128 to which the screw 120 is screwed. The cavity 126 allows free swinging of the gravity pointer 108 when such is desired. Also shown is the inner cavity 130 of the cup 102, defined by concave inner surface 118 which is adapted to the exterior shape of the shoulder knot 16 of an average horse 10. The cup 102 is mounted by an offset portion 132 so that the cup 102 can lay over the bony knot 16 without being held away by interference between the protractor 106 and the horse 10.

As shown in FIGS. 2, 3 and 4, the gauge 100 is adapted to be applied to the right side of a horse 10. Similar measurements may be desirable on the left shoulder, especially in animals which, because of some birth defect or prior injury, exhibit differing conformations on the two sides. For this instance a modified embodiment 200 can be employed which includes a right side cup 202 offset sidewardly by offset portion 203 and a left side cup 204 offset sidewardly by offset portion 205 for application to the right and left bony knots of the horse 10 respectively. In embodiment 200, the gravity pointer 206 is provided to the protractor 208 by means of a rivet 209 so that the tip 210 can point downwardly. The scale 212 of the protractor 208 is positioned on the inner surface 214 of an arculate portion 216 of the gauge 200 and since no back wall 128 is provided, the angle on the scale 212 indicated by the gravity pointer can be seen from either side. Angle indicia 218 are provided on both side surfaces 220 and 222 of the protractor.

The gravity pointer 208 rotates in a slot 224 formed in the lower portion 226 of the bone angle pointer 228 and thus is protected from binding contact with the horse 10 which otherwise might cause incorrect readings. As can be seen, the bone angle pointer 228 includes ridges 230 and 232 on opposite sides 234 and 236 thereof which correspond to ridge 125 and provide frictional contact with the horse no matter which side of the horse 10 is being measured. The sides 234 and 236 taper toward the tip 238 of the bone angle pointer 228 so that they are in general planar alignment with the respective offset cups 202 and 204. Other than providing a device which can measure both shoulder angles, and since the optional gravity pointer clamp is not provided so that the gauge 200 must be read when in place on the horse 10, the gauge 200 is used like the gauge 100.

The gauge of the invention has been described with reference to its preferred embodiment and to an advantageous modified form thereof. Changes in detailed construction of the gauge, such as may suggest themselves to one skilled in the art of measurement apparatus, upon exposure to the teachings herein, and the invention is to be limited only by the appended claims.

What is claimed is:

1. A gauge for determining the shoulder bone angle of a horse with respect to gravity including:
   a body having integral therewith, a protractor scale about an apex, a bone pointer on a first end thereof, and at least one joint cup on an opposite end thereof;
   a pivot at said apex; and
   a pointer pivoted for rotation about said pivot, said pointer having a pointer end and a back end, said pointer end being configured so that said pointer end has a larger moment about said pivot than said back end and having a pointer tip that is positioned adjacent said protractor scale for indicating the relative angle between said body and said pointer.

2. The gauge as defined in claim 1 wherein said joint cup is semi-spherically shaped having an concave horse contacting surface facing a predetermined direction with respect to said body.

3. The gauge as defined in claim 2 wherein said bone pointer includes at least one integral friction ridge for contact with the horse facing in said predetermined direction.

4. The gauge as defined in claim 3 wherein said protractor scale portion and said bone pointer portion of said body are generally in planar arrangement, said joint cup being offset therefrom in said predetermined direction.

5. The gauge as defined in claim 3 wherein said pivot includes adjustable friction means to releasably retain said pointer in a fixed angular relationship with respect to said protractor scale.

6. The gauge as defined in claim 1 wherein said body includes an arcuate portion having a concave arcuate surface and said protractor scale is located at least in part on said concave arcuate surface.

7. The gauge as defined in claim 6 having two joint cups, each of said joint cups being semi-spherically shaped and having an concave horse contacting surface, said concave horse contacting surfaces facing in opposite predetermined sidewardly directions with respect to said body.

8. The gauge as defined in claim 7 wherein said protractor scale portion and said bone pointer portion of said body are generally in planar arrangement, said joint cups being offset therefrom sidewardly in said predetermined directions.

9. The gauge as defined in claim 8 wherein said bone pointer includes at two integral friction ridges for contact with the horse, each facing in said opposite predetermined sidewardly directions with respect to said body.

10. The gauge as defined in claim 9 wherein said body has a predetermined width, said pointer being pivoted centrally in said predetermined width.

11. The gauge as defined in claim 10 wherein said body includes a pair of arcuate side surfaces on the opposite sides thereof adjacent said concave arcuate surface, said arcuate side surfaces having angle indicia for said protarctor scale thereon.

12. The gauge as defined in claim 11 wherein said bone pointer includes an outer tip, said bone pointer having side surfaces tapering toward said tip and being in general alignment with said ofset bone cups.

* * * * *